(12) United States Patent
Stangeland

(10) Patent No.: US 6,659,612 B1
(45) Date of Patent: Dec. 9, 2003

(54) DEVICE FOR USE IN EYESIGHT TESTING

(76) Inventor: Rolf Stangeland, Klinkenberggy. 16, Stavanger (NO), D-4008

( * ) Notice: Subject to any disclaimer, the term of this patent is extended or adjusted under 35 U.S.C. 154(b) by 0 days.

(21) Appl. No.: 09/913,210
(22) PCT Filed: Feb. 3, 2000
(86) PCT No.: PCT/NO00/00036
§ 371 (c)(1), (2), (4) Date: Oct. 30, 2001
(87) PCT Pub. No.: WO00/47106
PCT Pub. Date: Aug. 17, 2000

(30) Foreign Application Priority Data
Feb. 9, 1999 (NO) .................................... 990588

(51) Int. Cl.[7] ................................................ A61B 3/10
(52) U.S. Cl. ........................................................ 351/216
(58) Field of Search ................... 351/216, 217, 351/218, 227, 229, 230, 233, 41, 47, 57, 58, 63, 64, 65, 124, 159

(56) References Cited
U.S. PATENT DOCUMENTS

| | | | |
|---|---|---|---|
| 1,384,252 A | | 7/1921 | Giddens |
| 2,888,856 A | | 6/1959 | Marly |
| 4,549,792 A | * | 10/1985 | Dianitsch ..................... 351/63 |
| 5,486,879 A | | 1/1996 | Barnett |
| 5,596,378 A | | 1/1997 | Kelman |
| 6,022,105 A | * | 2/2000 | Lin ............................. 351/47 |

FOREIGN PATENT DOCUMENTS

| | | |
|---|---|---|
| DE | 76618 | 9/1893 |
| FR | 2481916 | 11/1981 |
| GB | 2293023 | 3/1996 |

* cited by examiner

*Primary Examiner*—George Manuel
(74) *Attorney, Agent, or Firm*—Andrus, Sceales, Starke & Sawall, LLP

(57) ABSTRACT

An eyesight tester for possibly finding short-sightedness, long-sightedness, etc. In the apparatus are included a number of lenses (34, 34a), differing with respect to lens power, embedded in at least one rotationally arranged wheel (24, 26) and located and distributed along an imaginary circle passing through an ocular (36, 38). The power value (for example −3) of each lens (for example 34a) is indicated on the side surface of the respective wheel (24) in such positions relative to the associated lens (34, 34a) that the power value (−3) of each single lens (for example 34a) will appear in a visible position (40, 41) when the associated lens (34a) is in the ocular (36, 38).

5 Claims, 8 Drawing Sheets

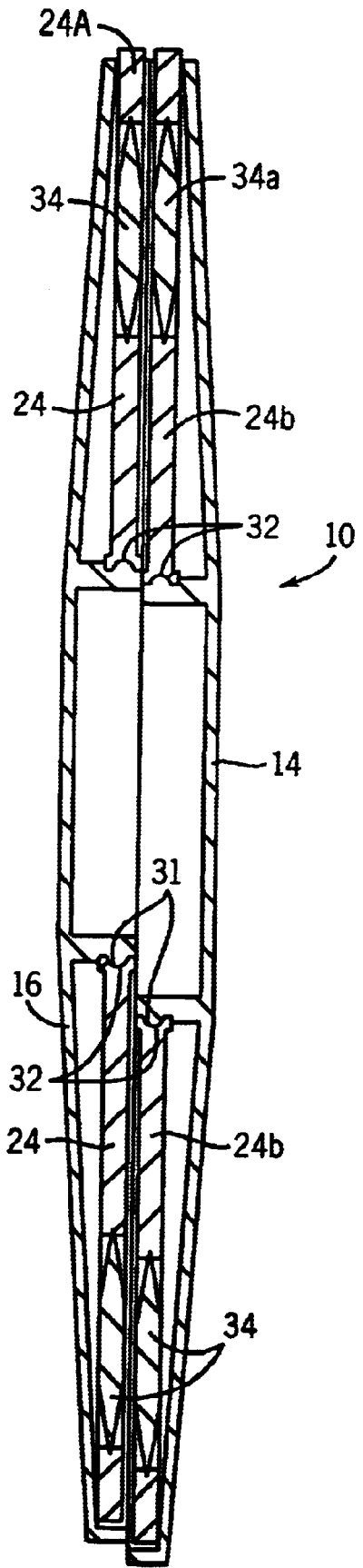

DEVICE FOR USE IN EYESIGHT TESTING

CROSS REFERENCE TO RELATED APPLICATION

The present application is the U.S. national stage application of International Application PCT/NO00/00036, filed Feb. 3, 2000, which international application was published on Aug. 17, 2000 as International Publication WO 00/47106 in the English language. The International Application claims priority of Norwegian Patent Application 19990588, filed Feb. 9, 1999.

SUMMARY OF THE INVENTION

This invention relates to a device for use in eyesight testing, so-called eyesight-tests, which device constitutes a means of the kind used to test whether a person needs spectacles/contact lenses, and also to determine the degree of short-sightedness, long-sightedness etc., which device comprises a number of lenses varying in power (refractive power).

Conventionally, eyesight is tested by the use of a letter chart, the so-called Snellen's chart, by which eyesight is measured in %.

Alternatively a standard spectacle case with loose spectacle lenses of different lens powers.

An automatic refractor of the type used by opticians, costs about NOK 100 000,-, a price level of a totally different order than that of eyesight testers of the kind that the present invention relates to. In this connection it may be mentioned that some people, including patients with reduced vision or visual defects of various kinds, often have an aversion to the use of large and bulky apparatus, such as autorefractors, and experience has shown that entirely satisfactory test results may be achieved for, for example, short-sightedness (myopia), long-sightedness (hypermetropia), and long-sightedness conditioned by old-age (presbyopia) by means of small, inexpensive aids, which may, through moderate modifications, also be employed in the testing of aberration of the cornea (astigmatism).

BRIEF DESCRIPTION OF THE INVENTION

The object of the present invention has been to provide a device of structurally simple configuration, which is easy to operate by the user him/herself, while effectively contributing, at the same time, because of its particular configuration, to the achieving of sufficiently accurate measuring results by means for eyesight testing of the kind in question.

Said purpose is realized according to the invention, in that a device for eye-testing of the kind specified in the claims is additionally configured so that it exhibits the features that appear from the claims.

An eye-tester configured in accordance with the invention, comprises in its most general embodiment, a support and at least one, preferably two wheels supported rotationally in the support and carrying lenses embedded in the wheel or mounted therein, of different powers/refractive powers, which lenses are distributed along a circular path, said support comprising cover elements for receiving and supporting the lens wheel, said cover elements exhibiting an opening positioned on said circular path, which the lenses may be brought to correspond with, one by one.

At least two partially encased lens wheels are normally received in one support, each wheel being enclosed in essentially two parallel cover elements, the two pairs of cover elements preferably being hinged together, so that the support may be folded together to occupy half its area when the eyesight tester is not in use, while at the same time the eyesight tester will be less sensitive to external shocks, impact etc. in this folded, strengthened condition. The hinge axis may extend perpendicular to an imaginary connecting line between the two eye pieces/oculars.

Besides the eye piece/ocular positioned on the common circular path of the distribution pattern of the lenses, the centre of said path coinciding with the point of rotation of the wheel, at least one cover element of each pair may have at least one further, transverse hole, recess or similar slot/configuration leading into the adjacent side surface/circumferential portion of the wheel, more specifically so that it could correspond with one of a number of specifications of lens power corresponding to the refractive power of the lens located in the eye piece. These lens power specifications may be suitably spaced apart along an imaginary circle directly on the side surface of the respective rotary wheel, and appear one at a time in said through hole in one cover element, or they may be positioned individually on projections from the wheel circumference and appear in edge recesses, whereby the specification of lens power corresponds, at all times, with the overlapping lens(es) present in the ocular in each case.

Said recess may be formed in the circumferential region of the pair of covers as an edge recess which permits—in addition to the task mentioned above—direct access to the wheel circumference portion of the respective wheel, so that by one finger one may turn the lens wheel in the wanted direction, while one eye is preferably positioned in front of the eye piece of the respective half of the support.

Each one of a number of specifications of lens powers corresponding to the refractive power of the lens present in the ocular/eye piece in each case, may be carried by a projection extending from the respective wheel circumference, which projection passes, by rotation of the wheel, through a narrow slot between adjacent outer edges of opposed cover elements. This narrow slot extends over part of the circumferential extent of each support half.

When the eyesight tester support is provided with two lens wheels, one for the right eye and one for the left eye, the two support halves, each comprising a pair of cover elements and a lens wheel supported rotationally between them, will be mirror symmetric about the hinge axis.

By expansion of the eyesight tester according to the invention so that it comprises two wheels in each support half, whereby the possibilities of attachment will be increased so that it will be possible to test for aberration of the cornea (astigmatism), the circular paths on the two parallel wheels of each support half, along which lenses, differing from each other in power, are distributed, may be positioned either centrically or eccentrically in relation to each other. By eccentric positioning of these circular paths of distribution, it will be somewhat easier to separate the individual wheel at the circumference where they project through their respective recesses in the circumferential region of the pair of cover elements, in connection with the advancement of the respective wheel. In this embodiment, two individual lenses, one from each circular pattern of distribution, may be brought to correspond with one another within the eye piece of the respective support half. With the eye piece located on one circle of distribution of one set of lenses, the other should, relative to this eccentrically positioned circle, intersect the former within the eye piece.

To allow the same eyesight tester to be used by several persons who have different distances between the eyes, the two support halves with one eye piece/ocular each, are arranged independently rotational relative to the hinge. For this purpose each support half is formed, along its circumference and over a part thereof, with a groove open radially outwards and engaged by a peripheral projecting strip along the edges of the hinge connecting to the support halves. The groove and the projecting strip is formed mutually complementary, so that along the opposite connecting edges of the hinge, the projecting strip cannot be pulled out radially from the groove of the respective support half, which groove may be closed at its ends. The projecting strip may have a radially inner bulb, which engages the radially inner, widest part of the groove, which joins a narrower groove section ending radially at the circumference. The engagement of the projecting strips in the grooves along parts of the circumferential edges of the support halves, is conveniently subjected to friction on surface portions resting on each other, so that the set distance of the eye pieces is kept constant until another person is to have his/her eyesight tested with the same apparatus.

By two concentric/eccentric lens wheels in each support half, two holes may be formed in each half for indications of lens powers, one from each hole. One of these holes is located at a distance (radius) from the point of rotation of the associated wheel, different from the corresponding distance (radius) of the other hole. This special embodiment requires, moreover, that the wheels themselves be transparent or at least have transparent portions, so that the indications of lens power of the wheel at the back (relative the ocular/eye) are not covered, but can be seen through the wheel/wheel portion in front.

BRIEF DESCRIPTION OF THE DRAWING

These and other details of the eyesight tester according to the invention will become more apparent in the following specification of the different non-limiting examples of embodiments in connection with the accompanying drawings, in which:

FIG. 8 is a radial section generally corresponding to FIG. 3, but showing the internal configuration of one support half of the embodiment according to FIG. 7;

FIG. 9 is a radial part sectional view along the section line IX—IX in FIG. 4;

DETAILED DESCRIPTION OF THE INVENTION

Figure 1:
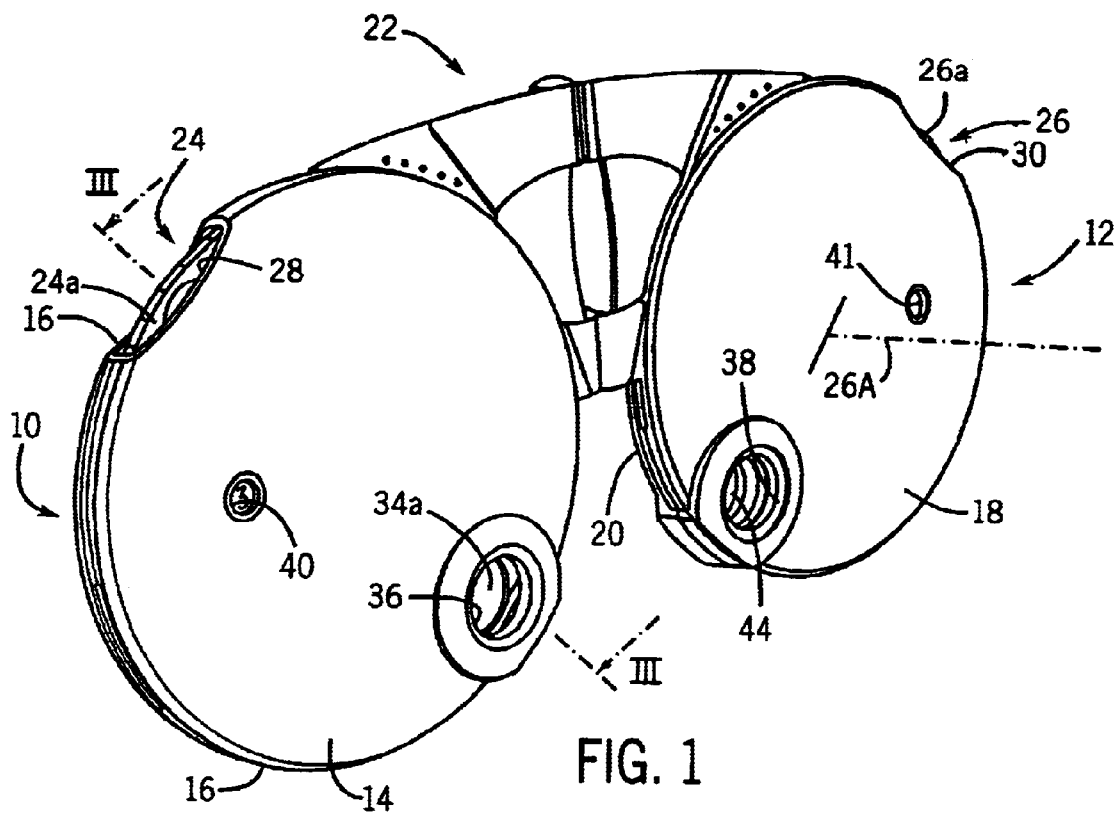
FIG. 1 shows, in perspective, a standard version of the present eyesight tester in its active position, formed of two support halves hinged together, each provided with a rotatable lens wheel and a stationary eye piece, and an opening arranged thereto for the indication of refractive power.

Reference is made to the drawings, first to FIGS. 1–4 which illustrate a first embodiment of the eyesight tester according to the invention, whereby one can test for short-sightedness and long-sightedness, for example. By means of the eyesight tester according to the two following embodiments, in which each support half has two wheels arranged thereto with lenses of different powers, one may for example test for aberration of cornea. These embodiments will be discussed later in connection with FIGS. 5–8.

In FIGS. 1–4 the reference numerals 10 and 12 indicate two support halves hinged together, each comprising a pair of cover elements 14, 16 and 18, 20 overlapping in pairs. This shared hinge structure is defined by 22. All these main parts may be produced from suitable plastic materials. The hinge may have two stable positions, one open active position, FIGS. 1 and 2, and a folded, inactive position, FIG. 4. In its folded inactive position the support structure of the eyesight tester occupies minimal space and is less vulnerable than in its unfolded condition.

Figure 2:
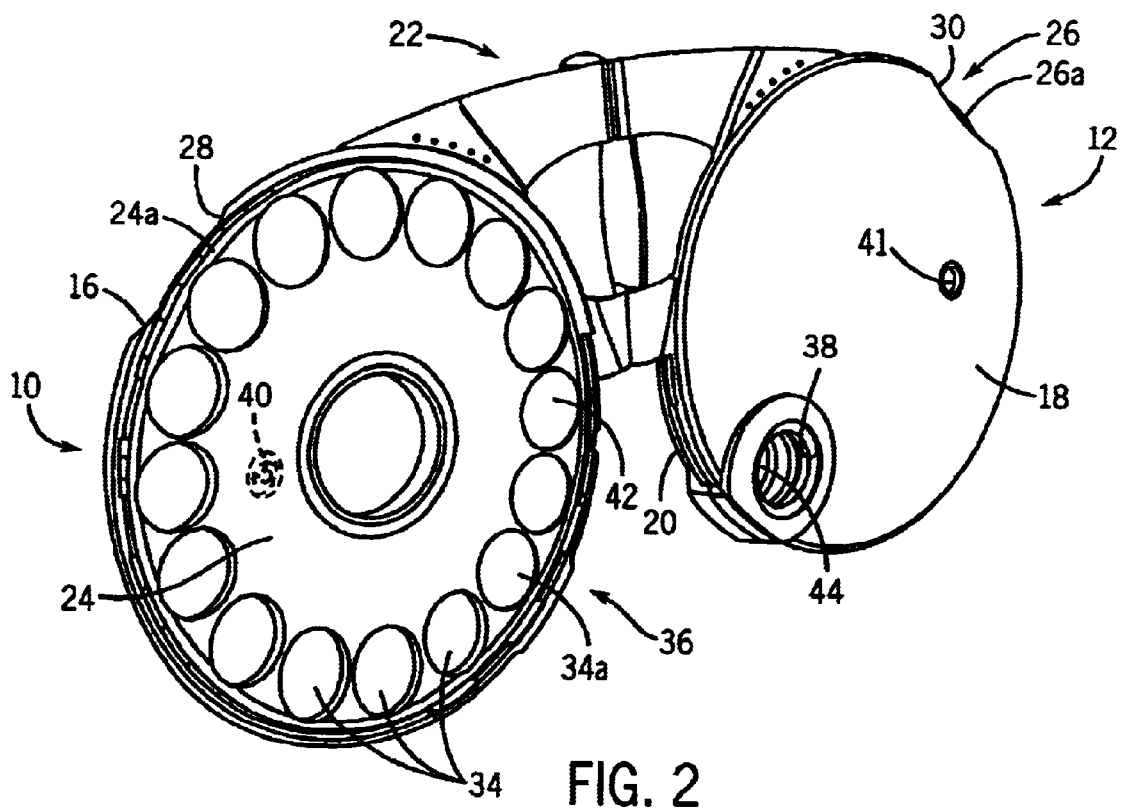
FIG. 2 corresponds to FIG. 1, but here the cover of one support half is removed to show the rotatable wheel located within with a number of lenses of different refractive powers, distributed along a circular path adjacent to the circumference of the wheel and concentric therewith.

Between the two cover elements 14, 16 and 18, 20 of each support half 10, 12 are rotatably supported wheels 24 and 24, see in particular FIG. 2, projecting from the cover elements 14, 16 and 18, 20, respectively, in the radial direction by a wheel circumference portion 24*a* and 26*a*, respectively, through a recess 28, 30 in the common circumferential area of the cover elements overlapping in pairs.

Figure 3:
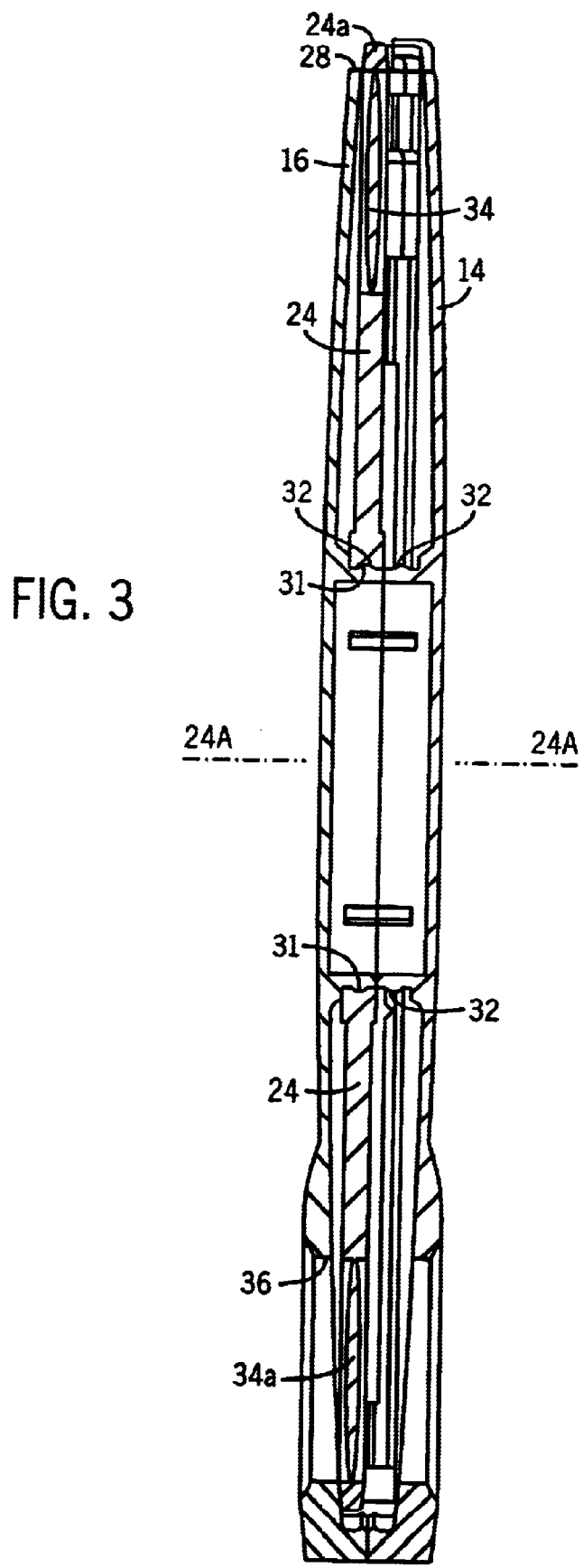
FIG. 3 is a radial section corresponding to the line III—III in FIG. 1 through one support half comprising two cover elements with an intermediate lens wheel.

Each wheel 24 or 26 has the form of an annular specially profiled disc, FIG. 3, whose inner circular circumferential surface is formed with a circular groove 31, which is engaged, in a glidingly displaceable manner, by a complimentarily formed bulb 32 on an adjacent internal hub, FIGS. 3 and 8.

Lenses 34 differing in refractive powers are distributed along an imaginary circle which is centric with respect to the axis of rotation 24A, 26A of the wheel 24, 26.

Each support half 10, 12 has an eye piece, indicated by 36 and 38, respectively. Fittings around each eye piece are exclusively of an aesthetic nature and without any technical significance to the present invention, each hole 36, 38 representing the most suitable point on the eyesight tester for placing each eye in the testing of eyesight right opposite, for example individually, a number of lenses 34, 34*a* whose powers/refractive powers differ from one another, so that each set of lenses of one wheel may comprise lenses of steps of 0,5 dioptres. From 0 to −5 dioptres on one half of the wheel—180°—and from 0 to +5 dioptres on the other half of the wheel, all together for example 22 lenses distributed along the circumference of one wheel.

In addition to the lenses 34, 34*a* there should be an opaque but translucent area 42, 44 corresponding to a lens area in size and location, so that it will be possible to block one eye.

In the shown embodiment of the eyesight tester, the lenses 34, 34*a* should conveniently be embedded in the respective wheels 24 or 26, see in particular FIG. 3. Both the wheel 24 and the lenses may possibly be moulded of the same material.

Figure 5:
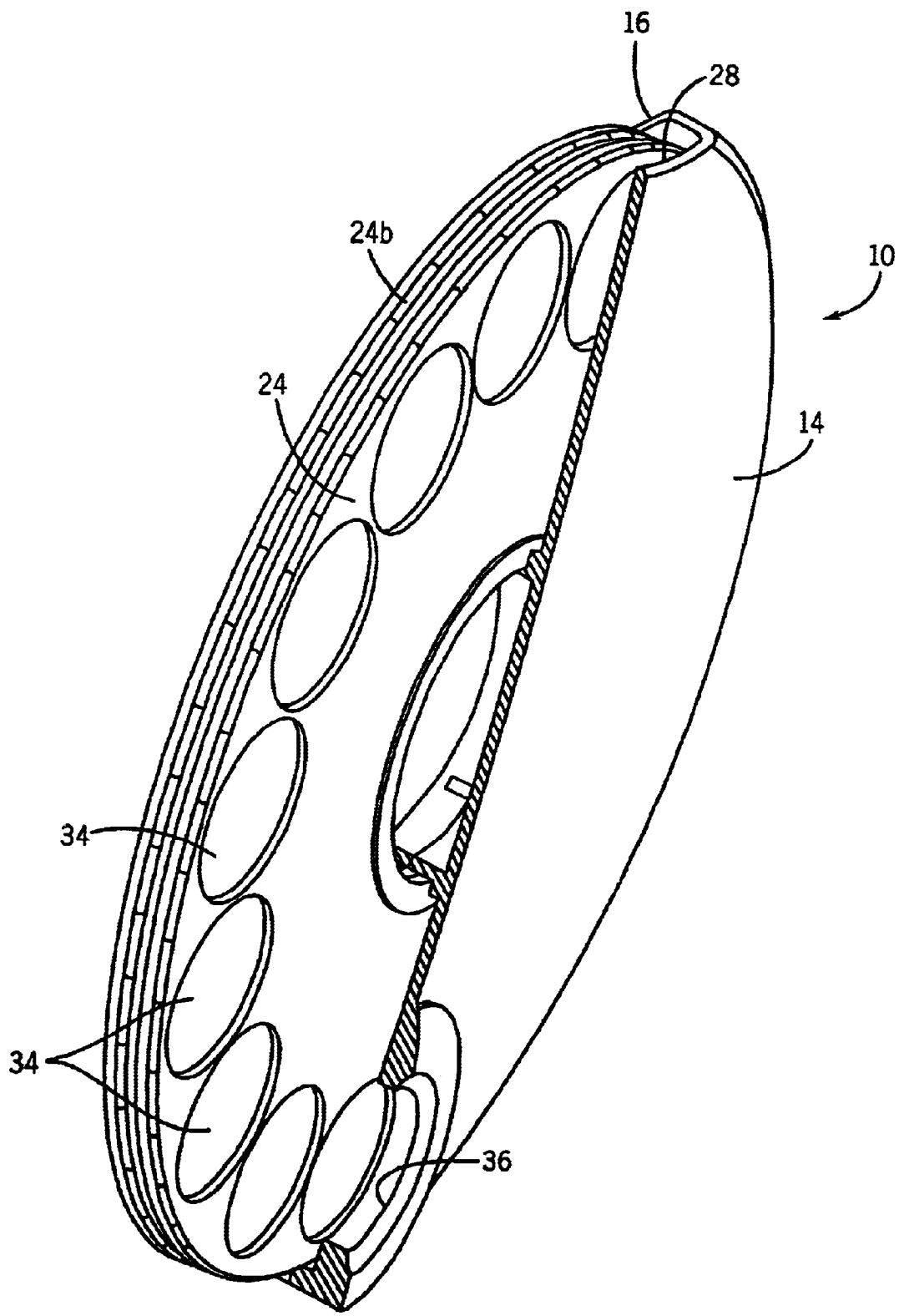
FIG. 5 shows a partially cut support half of a second embodiment, in which the support of the eyesight tester comprises two parallel wheels in each support half, which wheels, in the embodiment suggested in FIG. 5, are mutually centric and identical in size and shape.
Figure 6:
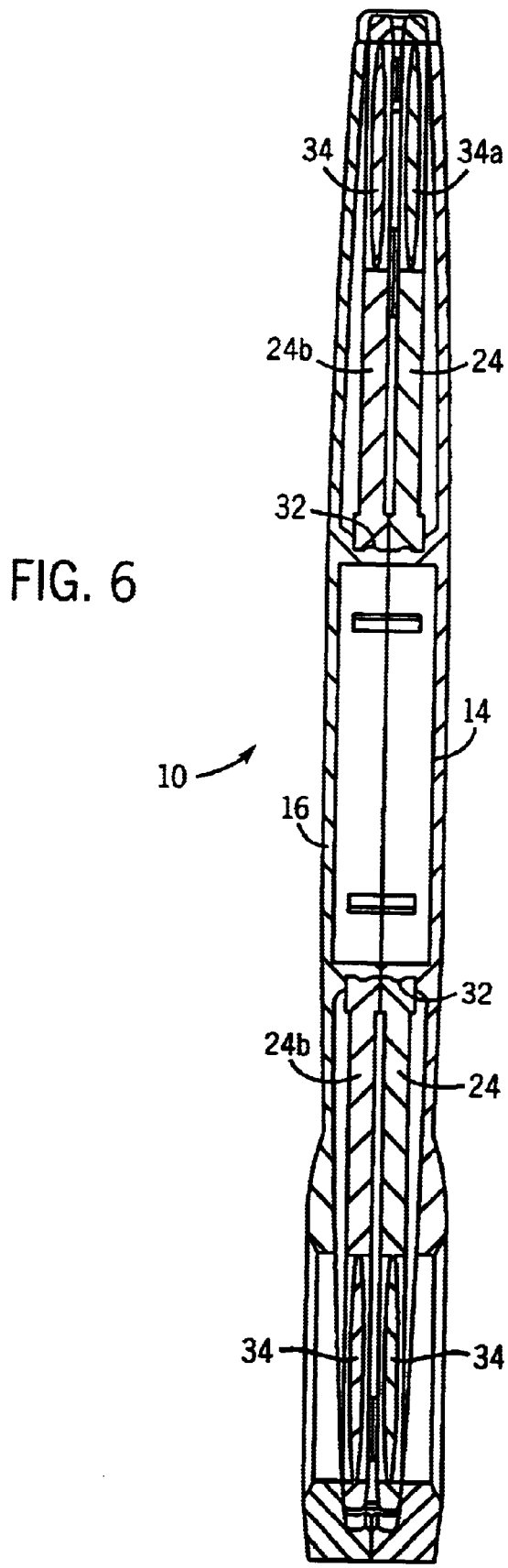
FIG. 6 shows a radial section through the support half with two wheels according to FIG. 5.

A common feature of two further embodiments of the invention consists in the use of two overlapping wheels 24, 24*b* in each support half of the eyesight tester according to the invention, wherein the two wheels 24, 24*b* are independently rotatable relative to one another, and—in FIGS. 5 and 6—arranged centrically to one another. Thereby two lenses 34—one from each of the two wheels—may be brought to overlap one another within the eye piece 36, for example with the purpose of testing for aberration of the cornea.

Figure 7:
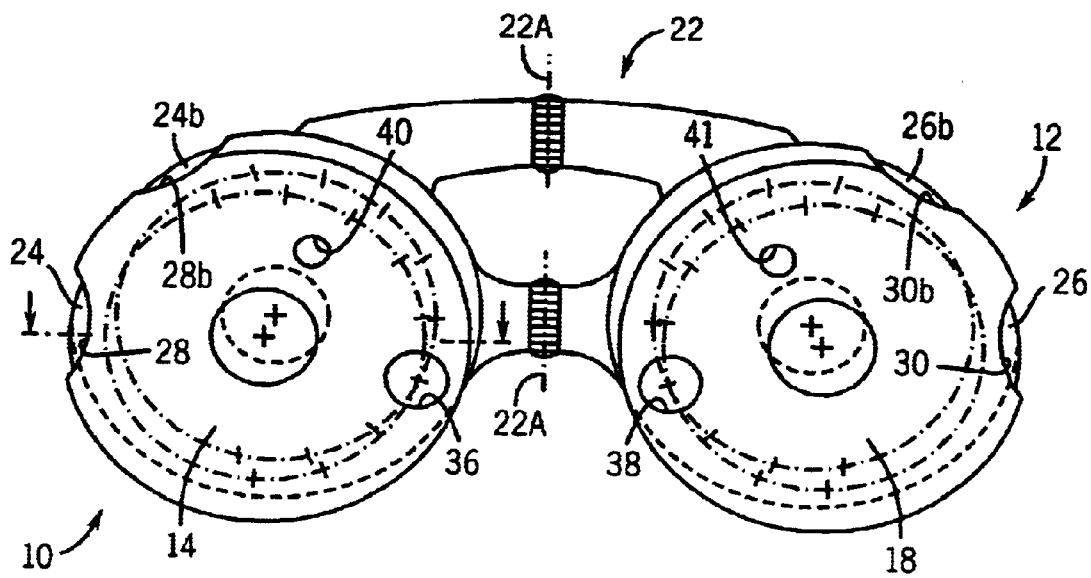
FIG. 7 shows a view of a third embodiment, seen straight from the front, this embodiment also provided with two lens wheels in each support half, but here the two wheels are placed eccentric to one another, so that it will be easier to operate the projecting circumferential portion of either wheel, without touching the projecting circumferential portion of the other wheel.

In the embodiment according to FIGS. 7 and 8 the two wheels 24, 24*b*, which partially overlap one another within one support half of the eyesight tester, are supported eccentric to each other. This provides advantages in the advancing of one wheel relative to the other by the projecting outer circumferential portion of the respective wheel, in that by this eccentric positioning of the wheels, it will be more difficult to mistake their projecting peripheral operating portions, where recesses are formed in the common circumferential region of the pair of cover elements.

As appears from FIG. 7, one lens distribution circle will have to intersect the other (eccentric) circle within the respective eye piece 36, 38.

In the two embodiments last mentioned, FIGS. 5 and 6 and 7 and 8, respectively, the same references have been used for identical and similar parts, compared to the parts of the preceding FIGS. 1–4.

In one possible embodiment one wheel may comprise 22 lenses 34, 34*a*, while the other wheel may be used to test for example for aberration of the corneas, wherein the refractive power of the lenses may vary from 0 to −5 dioptres with steps of for example 0,25 dioptres.

In use the relevant lens wheel is turned until the lens, for example 34A, through which one can have the sharpest vision with the eye positioned at the eye piece 36 (or 38). The lens power is read off in the hole 40 (or 41) and may be for example −3 for the lens 34*a* in the eye piece 36. It will be understood that the wheel surface 24, which appears from FIG. 2, will be marked with the lens power values (such as −3 for 34*a*), which will appear in the small hole 40 (or 41) while, at the same time, the associated lens 34 is located in the eye piece 36 (or 38).

The embodiment of the eyesight tester according to FIGS. 5 and 6 or FIGS. 7 and 8 may be constructed for a way of operating, in which the uppermost wheels 24*b*, 26*b* are first set to power 0, after which the lowermost wheels 24, 26 are set to the best power first, corrections possibly being made later to test for aberration of the cornea, by adjusting the uppermost wheels 24*b*, 26*b* until vision is optimal. Then the result is read off. The eyesight tester may possibly be manipulated by the user, who may spend a very long time carrying out the test, which may also be extended to comprise testing of depth vision, colour vision etc.

With a magnifying lens (not shown) in the ocular (eye piece with lens, for example 36, 34*a*) it will be possible to reduce the size of the lenses of the wheels and obtain greater accuracy in the measuring with steps of 0,25 dioptres.

Figure 4:
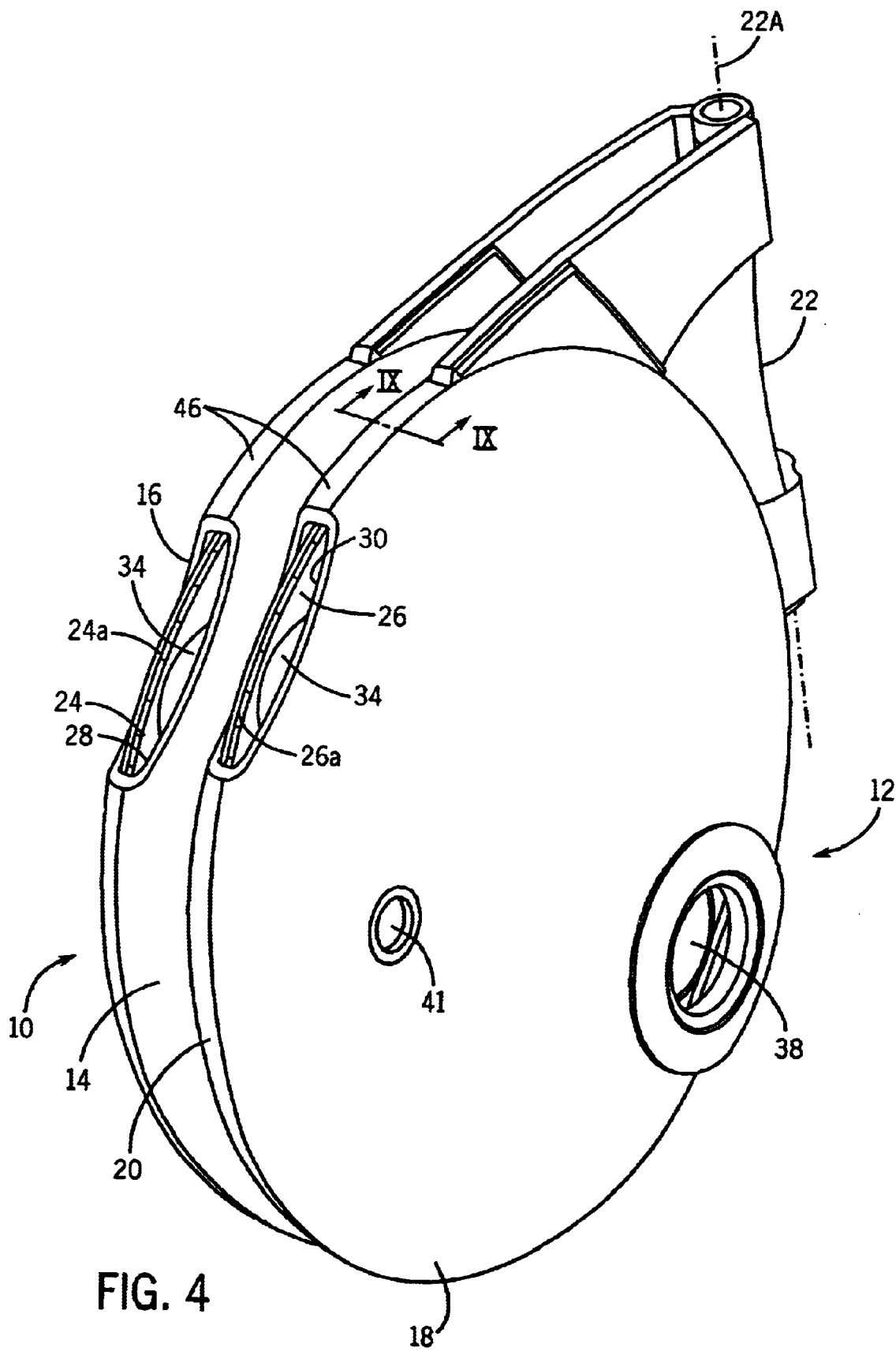
FIG. 4 is a perspective view of the eyesight tester in FIG. 1 in its folded-up, idle position.

In FIG. 9 which is a radial sectional view along the line IX—IX in FIG. 4, there is shown a possible ability of the circumference of each of the support halves 10, 12 to rotate relative to the hinge 22, along a suitable continuous part of the circumference of said support halves. By such a rotatability the two eye pieces/oculars 36, 38 may be brought to be mutually approaching/separating, for an eyesight tester to be suited for several persons of different eye distances.

An elongate, curved projecting strip 44 extending along each connecting edge of the hinge blades, has an outer thickened part, which displaceably engages, with friction, a radially inner groove portion of a complementary cross-sectional form, of a groove 46 with the cross-sectional shape of an inverted T, formed between a pair of cooperating cover elements 18, 20, at the circumference thereof. The groove 46 may have closed ends. The projecting strip 44 of the hinge 22 engaging the groove 46 cannot fall out of the groove 46, and the rotatable connection between the hinge on the one hand and each of the support halves 10, 12 on the other hand is thus permanently connected. By clockwise rotation of the support half comprising the pair of covers 18,20, FIG. 4, the ocular/eye piece 38 will move away from the hinge axis 22A. So would the ocular 36 of the pair of cover elements 14,16 by anti-clockwise rotation, in the unfolded position, FIG. 1, resulting in an increased distance between the oculars 36, 38.

Figure 10:
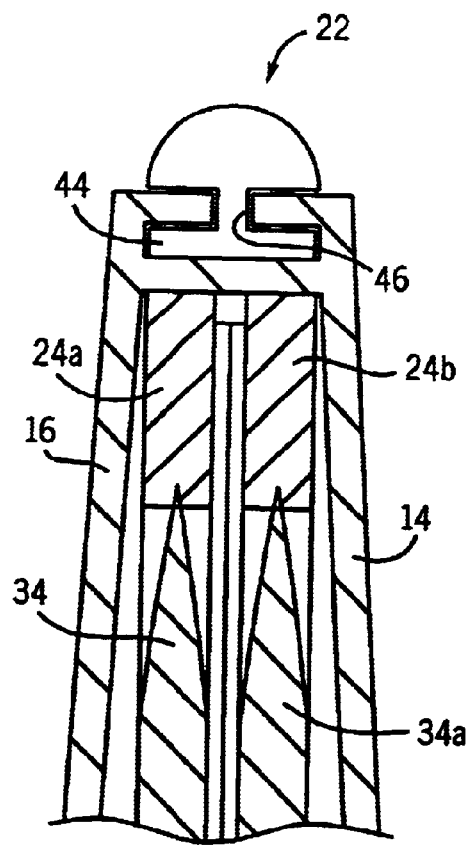
FIG. 10 is a part sectional view, corresponding to FIG. 9, on a larger scale, and showing an embodiment with two parallel lens wheels.

FIG. 10 shows a partial cross-sectional view on a larger scale, corresponding to FIG. 9, in which the support half 14,16 encloses two coaxial lens wheels 24, 24*b*, and in which the lenses, which are indicated by 34, 34*a*, are embedded in the respective wheel 24, 24*b* near the wheel circumference. The joined circumferential portions of the cover elements 14, 16 are formed with a groove 46 with the cross-sectional shape of an inverted T, which is displaceably engaged by a complimentarily shaped portion 44 of the hinge 22.

Figure 11:
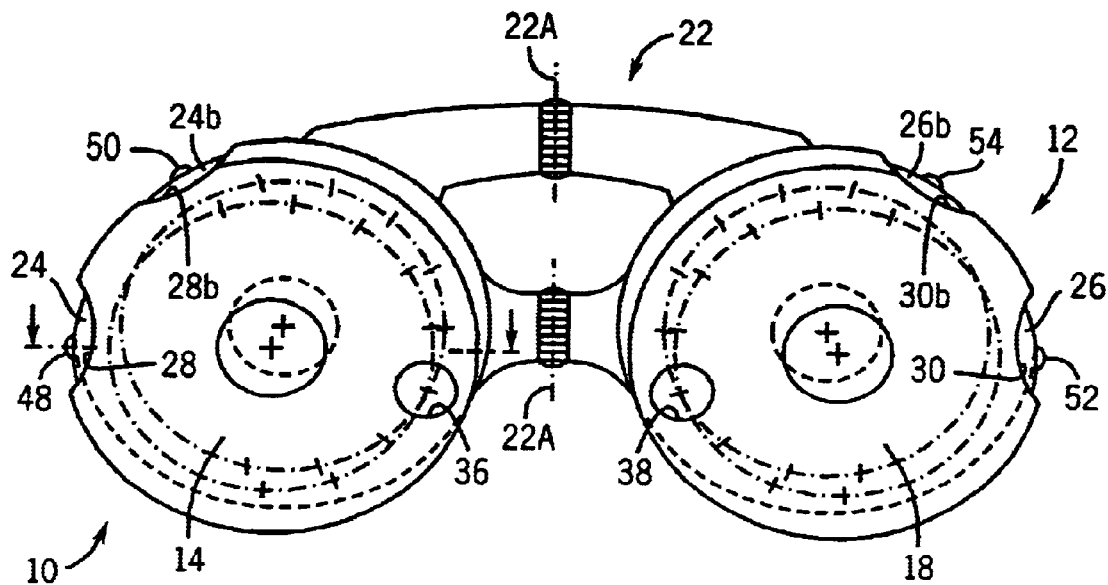
FIG. 11 corresponds to the front view according to FIG. 7, but shows a fourth embodiment with two eccentrically arranged wheels in each support half, the circumferences of the wheels being provided with projecting, rounded tongues which project individually in the area of the respective edge recess in the circumferential portion of the pair of covers.

In the embodiment according to FIG. 11 there are arranged, in each support half 10, 12, two wheels 24, 24*b* and 26, 26*b*, the wheels of each pair of wheels being arranged eccentric to one another.

As in FIG. 7 each support half 10 and 12 are formed with two edge recesses, 28,28*b* and 30,30*b*, respectively, at their circumferences.

Each wheel 24, 24*b*, 26, 26*b* is provided with a number of radially projecting tongues, projections 48, 50, 52, 54, of which one can be seen in each edge recess, 28, 28*b*, 30, 30*b*, respectively, each one carrying an indication of lens powers, indicated only for the projection 50, indicating −3, corresponding to one of the lenses located in the eye piece 36.

These radial projections are carried by the circumference of the respective wheel 24, 24*b*, 26, 26*b*, and do not project beyond the outer circumference of the respective support half 10, 12.

Figure 12:
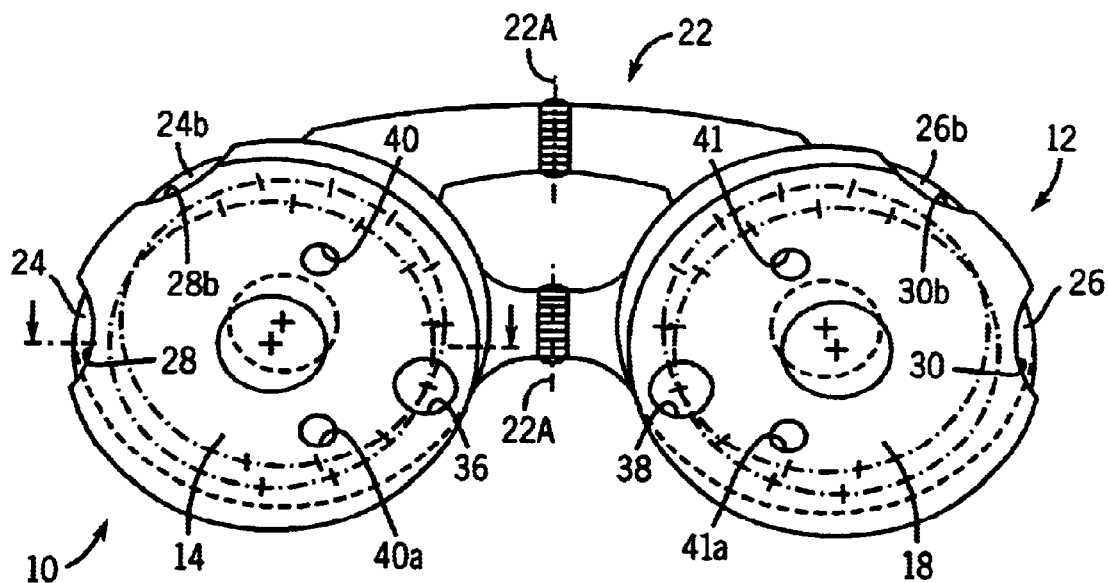
FIG. 12 is a front view corresponding to FIGS. 7 and 11, but shows a fifth embodiment, in which there are formed in the front cover element two through holes for the indications of lens power, which embodiment assumes that at least the front wheel or portions thereof is transparent, so that the indications of lens power of the wheel behind, passing their hole one by one, are not covered.

In FIG. 12, in a front view corresponding to FIGS. 7 and 11, is visualized a further embodiment in which there are formed, in each front cover element 14, 18, two through holes 40, 40*a* and 41, 41*a* to disclose the lens power indications on the outward wheel surface, corresponding to the mutually overlapping lenses of two wheels, made visible simultaneously in the eye pieces 36, 38. Thereby, the front wheels 24b and 26b must be transparent, either entirely or in the areas of the imaginary circular paths of distribution of the rear wheels 24 and 26, along which are placed the lens power indications of the wheels last mentioned, and which must not be covered and made invisible by the front wheels 24b and 26b.

What is claimed is:

1. A device for use in testing eyesight for the purpose of possibly finding short-sightedness, long-sightedness, etc., in the form of a simple means, a so-called eyesight tester, comprising a number of lenses (34, 34a) of different refractive powers, which may be brought by an ocular device (36; 38) into position in front of the eye to be tested, said device further comprising a support (10,12) including two support parts (10 and 12) each formed for rotationally supporting at least one wheel (for example 24b) of a preferably round circumference, along, which said lenses (34, 34a) are positioned, distributed along at least one imaginary circle, said ocular device (36; 38) being located on this imaginary circle, so that one lens (34, 34a) of a respective wheel (24, 24b) at a time is positioned within said ocular device (36; 38) by stepped turning of said wheel, and wherein provisions have been made to make visible a lens power indication (for example −3) on the wheel corresponding to the lens (34a) or mutually overlapping lenses appearing simultaneously within the ocular (36; 38), said lens power indications being carried by the respective wheel, preferably distributed along imaginary circles, characterized in that said two parts (10 and 12) of the eyesight tester support (10,12) are hinged together, said hinge (22) exhibiting such flexibility as to allow the support (10,12) to be folded about the hinge axis to occupy a double folded, inoperative position, in which the two support parts (10 and 12) overlap one another.

2. A device as set forth in claim 1, characterized in that the circumference of said wheel (24, 24b, 26, 26b) is provided with radially directed projections (48, 50, 52, 54) each carrying a lens power indication (for example −3), said lens power indications appearing in said edge recesses (28, 28b, 30, 30b) simultaneously with at least one lens appearing in the ocular (36, 38).

3. A device as set forth in claim 2, characterized in that the hinge (22) has two stable positions, one open position in which its two hinge parts are orientated in the continuation of one another, corresponding to the position of use of the eyesight tester, and a folded position in which the hinge parts substantially overlap each other, and wherein, in the latter hinge position, the support parts (10 and 12) also overlap one another substantially.

4. A device as set forth in claim 1, characterized in that each support part (10, 12) is formed, at least over a portion of its circumference, with a groove (46) which is open outwardly in a radial direction, said groove (46) having a larger width at its bottom than at its opening at said circumference, and accommodating displaceably therein a correspondingly shaped projection of the adjacent edge of said hinge (22) foldably interconnecting the support parts (10, 12).

5. A device as set forth in claim 1, characterized in that each support part (10, 12) is rotationally connected to the hinge (22), the arrangement being such that the distance between the oculars (36, 38) can be changed.

* * * * *